(12) United States Patent
Chen et al.

(10) Patent No.: US 8,614,336 B2
(45) Date of Patent: *Dec. 24, 2013

(54) PROCESS FOR PREPARING N-METHYL-N-HYDROXYL-3-(1-NAPHTHYLOXY)-3-(2-THIENYL)PROPYLAMINE DERIVATIVE

(75) Inventors: Bo-Fong Chen, Taoyuan (TW);
Jinun-Ban Yeh, Taoyuan (TW);
Wei-Chyun Wong, Taoyuan (TW)

(73) Assignee: SCI Pharmtech, Inc. (TW)

( * ) Notice: Subject to any disclaimer, the term of this patent is extended or adjusted under 35 U.S.C. 154(b) by 590 days.

This patent is subject to a terminal disclaimer.

(21) Appl. No.: 12/718,289

(22) Filed: Mar. 5, 2010

(65) Prior Publication Data

US 2010/0234620 A1     Sep. 16, 2010

Related U.S. Application Data

(63) Continuation-in-part of application No. 12/402,740, filed on Mar. 12, 2009, now Pat. No. 8,148,549.

(51) Int. Cl.
*C07D 333/10*     (2006.01)

(52) U.S. Cl.
USPC ........................................... 549/75

(58) Field of Classification Search
USPC .......................................... 549/75
See application file for complete search history.

(56) References Cited

U.S. PATENT DOCUMENTS

| | | | |
|---|---|---|---|
| 5,023,269 A | 6/1991 | Robertson et al. | |
| 7,538,232 B2 * | 5/2009 | Butchko et al. | 549/75 |
| 8,148,549 B2 * | 4/2012 | Chen et al. | 549/75 |
| 2008/0171887 A1 * | 7/2008 | Pospisilik et al. | 549/72 |

OTHER PUBLICATIONS

Patani, et al., Chem. Rev., 1996, 96, pp. 3147-3176, esp. p. 3149.*

* cited by examiner

*Primary Examiner* — Susannah Chung
(74) *Attorney, Agent, or Firm* — Berliner & Associates

(57) ABSTRACT

The present invention provides a process for preparing a N-methyl-N-hydroxyl-3-(1-naphthyloxy)-3-(2-thienyl)propylamine compound. The present invention also provides a process for preparing (S)-(+)-N-methyl-3-methyl-3-(1-naphthyloxy)-3-(2-thienyl)propylamine with higher yield and low treatment cost, which includes the preparation of the N-methyl-N-hydroxyl-3-(1-naphthyloxy)-3-(2-thienyl)propylamine compound.

19 Claims, No Drawings

PROCESS FOR PREPARING N-METHYL-N-HYDROXYL-3-(1-NAPHTHYLOXY)-3-(2-THIENYL)PROPYLAMINE DERIVATIVE

CROSS-REFERENCE TO RELATED APPLICATION

This application is a continuation-in-part of, and claims the benefit of patent application Ser. No. 12/402,740 filed Mar. 12, 2009 now U.S. Pat. No. 8,148,549 which is incorporated for reference in its entirety.

BACKGROUND OF THE INVENTION

1. Field of the Invention

The present invention relates to a process for preparing (S)-(+)-N-methyl-3-(1-naphthyloxy)-3-(2-thienyl)propylamine by using a chiral methylhydroxylaminopropanol compound as an intermediate. More particularly, the preparation of (S)-(+)-N-methyl-3-(1-naphthyloxy)-3-(2-thienyl)propylamine includes an improved process for preparing a N-methyl-N-hydroxyl-3-(1-naphthyloxy)-3-(2-thienyl)propylamine compound.

2. Description of Related Art (S)-(+)-N-methyl-3-(1-naphthyloxy)-3-(2-thienyl)propylamine (Duloxetine®) is an antidepressant drug developed by Eli Lilly and Company, Inc. Various methods have been reported to prepare Duloxetine®. For example, U.S. Pat. No. 5,023,269 discloses a process as shown in the following scheme:

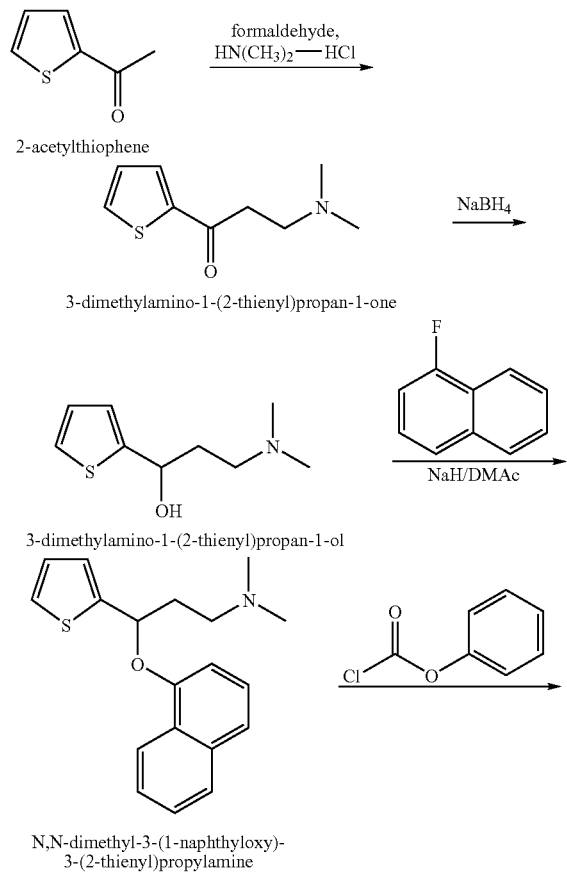

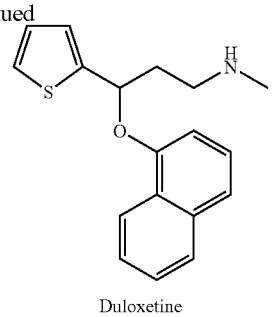

Duloxetine

In this example, 2-acetylthiophene is used as the starting material for reacting with formaldehyde and dimethylamine to form a Mannich product, namely 3-dimethylamino-1-(2-thienyl)propan-1-one. A hydride reduction is performed on this propanone to form corresponding 3-dimethylamino-1-(2-thienyl)propan-1-ol. The resulting propanol is then reacted with fluoronaphthalene to form N,N-dimethyl-3-(1-naphthyloxy)-3-(2-thienyl)propylamine. Subsequently, racemic Duloxetine® is obtained by demethylation of this propylamine. In this process, the yield of demethylation is very low, about 41%. In addition, Duloxetine® produced via this route is racemic.

Accordingly, U.S. Pat. No. 7,538,232 discloses a process to preserve the chiral integrity by using a mixture of organic solvents. However, different types of organic solvents used in the process for the preparation of Duloxetine® increase cost for subsequent treatment. In addition, the usage of mixed organic solvents also is disadvantageous to meet the developing trends of environmental protection. Therefore, it still remains a need to provide a process for preparation of chiral Duloxetine®.

SUMMARY OF THE INVENTION

In light of the above-mentioned drawbacks of the prior art, the present invention provides an improved process for preparing a N-methyl-N-hydroxyl-3-(1-naphthyloxy)-3-(2-thienyl)propylamine compound of formula (III), including a reaction of a (S)-methylhydroxylaminopropanol compound of formula (II) with KOR$_1$ and halonaphthalene in DMSO,

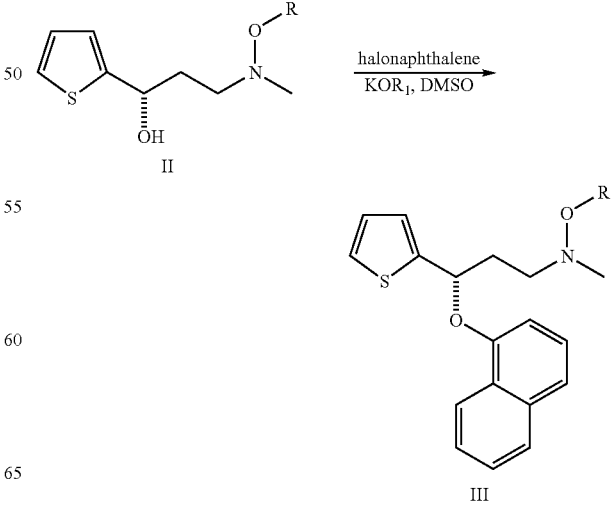

wherein R is a hydrogen atom, $C_{1-8}$ alkyl or $C_{6-10}$ aryl; $R_1$ is $C_{1-6}$ alkyl; and halo is F, Cl, Br or I.

In the present invention, the process is carried out at a temperature ranged from 10° C. to 110° C. Further, an amount of the halonaphthalene used in the process ranges from 1.5 to 7.0 equivalents based on 1.1 equivalent of the $KOR_1$.

The present invention also provides a process for preparing (S)-(+)-N-methyl-3-(1-naphthyloxy)-3-(2-thienyl)propylamine (Duloxetine®) with higher yield and lower treatment cost by using the (S)-methylhydroxylaminopropanol compound of formula (II) as an intermediate and $KOR_1$ in DMSO.

In the present invention, the process for preparing Duloxetine includes steps of:

(i) performing a Mannich reaction of 2-acetylthiophene, formaldehyde and a methylhydroxylamine compound of formula, $HNCH_3(OR)$, to form a substituted amino ketone of formula (I);

(ii) reducing the substituted amino ketone of formula (I) enatioselectively to a (S)-methylhydroxylaminopropanol compound of formula (II);

(iii) reacting the (S)-methylhydroxylaminopropanol compound of formula (II) with $KOR_1$ and halonaphthalene in DMSO to form a N-methyl-N-hydroxyl-3-(1-naphthyloxy)-3-(2-thienyl)propylamine compound of formula (III); and (iv) performing an N,O-cleavage reaction of the N-methyl-N-hydroxyl-3-(1-naphthyloxy)-3-(2-thienyl)propylamine compound of formula (III) to form (S)-(+)-N-methyl-3-(1-naphthyloxy)-3-(2-thienyl)propylamine (Duloxetine®),

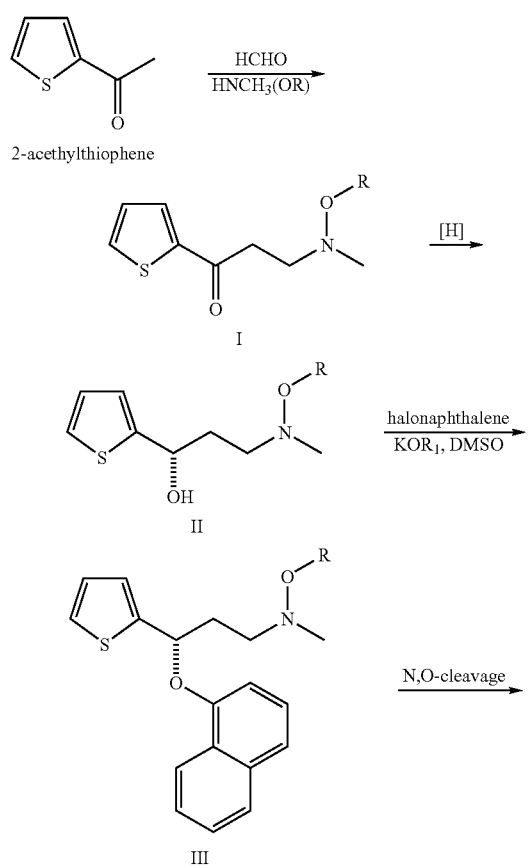

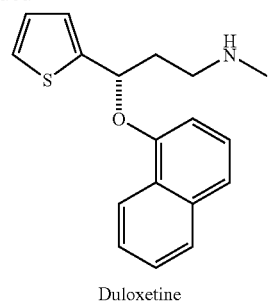

Duloxetine wherein R is a hydrogen atom, $C_{1-8}$ alkyl or $C_{6-10}$ aryl; $R_1$ is $C_{1-6}$ alkyl; and halo is F, Cl, Br or I.

DETAILED DESCRIPTION OF PREFERRED EMBODIMENTS

The following illustrative embodiments are provided to illustrate the disclosure of the present invention. These and other advantages and effects can be apparently understood by those in the art after reading the disclosure of this specification. The present invention can also be performed or applied by other different embodiments. The details of the specification may be on the basis of different points and applications, and numerous modifications and variations can be devised without departing from the spirit of the present invention.

The present invention provides a methylhydroxylaminopropanol compound of formula (II) in an optical active form:

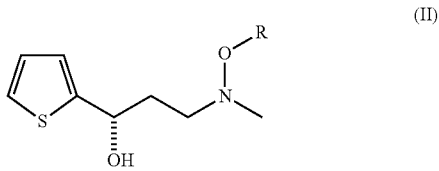

(II)

wherein R is a hydrogen atom, $C_{1-8}$ alkyl or $C_{6-10}$ aryl. Furthermore, the absolute configuration of the chiral center is S.

R in the above formula (II) is preferably $C_{1-4}$ alkyl, and is more preferably methyl.

Furthermore, the present invention provides a process for preparing (S)-(+)-N-methyl-3-(1-naphthyloxy)-3-(2-thienyl) propylamine (Duloxetine®), wherein the (S)-methylhydroxylaminopropanol compound of formula (II) is used as an intermediate. The process of the present invention is summarized in Scheme 1.

Scheme 1

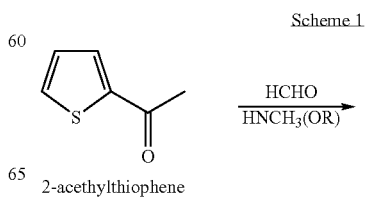

2-acethylthiophene

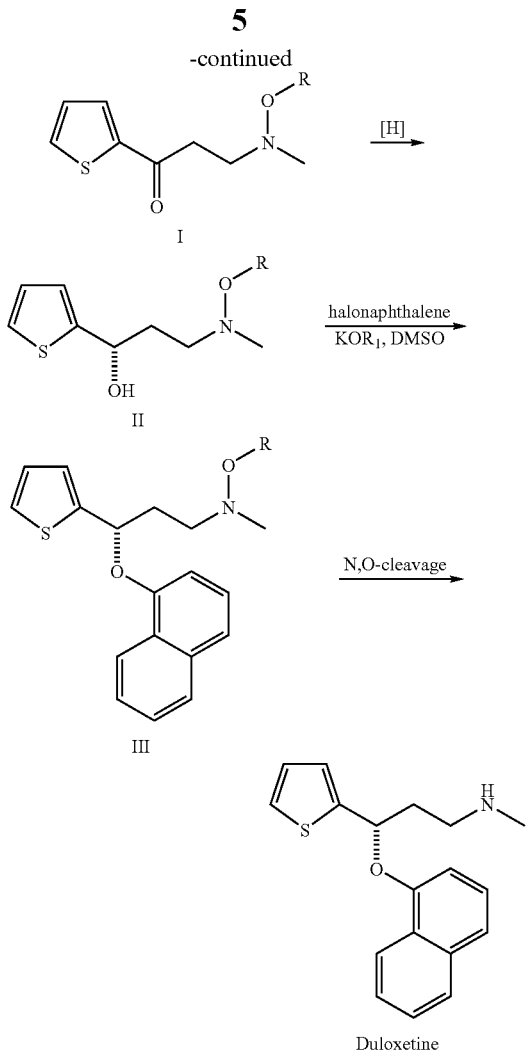

In Scheme 1, R is a hydrogen atom, $C_{1-8}$ alkyl or $C_{6-10}$ aryl.

In more details, the process of the present invention includes steps of:

(i) performing a Mannich reaction of 2-acetylthiophene, formaldehyde and a methylhydroxylamine compound of formula, $HNCH_3(OR)$, to form a substituted amino ketone of formula (I);

(ii) reducing the substituted amino ketone of formula (I) enatioselectively to a (S)-methylhydroxylaminopropanol compound of formula (II);

(iii) reacting the (S)-methylhydroxylaminopropanol compound of formula (II) with $KOR_1$ and halonaphthalene in DMSO to form a N-methyl-N-hydroxyl-3-(1-naphthyloxy)-3-(2-thienyl)propylamine compound of formula (III); and (iv) performing an N,O-cleavage reaction of the N-methyl-N-hydroxyl-3-(1-naphthyloxy)-3-(2-thienyl)propylamine compound of formula (III) to form Duloxetine.

The step (i) of the process is carried out at a temperature ranged from 15° C. to 90° C., preferably 40° C. to 80° C., and more preferably 50° C. to 70° C. The substituted amino ketone of formula (I) obtained in the step (i) is either as a free form or as an acid addition salt.

The reduction of the substituted amino ketone of formula (I) in the step (ii) is performed by asymmetric reduction, and the resulting optically active form of the (S)-methylhydroxylaminopropanol compound of formula (II) is obtained. The optically active form can be obtained via asymmetric hydrogenation using a catalyst with chiral ligands or a hydride with chiral ligands.

In one preferred embodiment, reduction of the substituted amino ketone of formula (I) in the step (ii) is carried out in a mixture of an alcohol such as methanol and a base such as potassium tert-butoxide, in the presence of a catalyst that includes an enantiomer-enriched bidentate phosphorus-containing ligand, a transition metal and a diamine, preferably a chiral diamine, such as $RuCl_2((R)-3,5-xylylBINAP)$ ((2R)-DAIPEN). The reaction mixture is hydrogenated at predetermined pressure to yield the (S)-methylhydroxylaminopropanol compound of formula (II) with high ee value.

The reaction of the (S)-methylhydroxylaminopropanol compound of formula (II) with halonaphthalene to form a N-methyl-N-hydroxyl-3-(1-naphthyloxy)-3-(2-thienyl)propylamine compound of formula (III) in the step (iii) is carried out by using an appropriate base in a suitable aprotic solvent.

In one preferred embodiment, the (S)-methylhydroxylaminopropanol compound of formula (II) is reacted with fluoronaphthalene in DMF by using sodium hydride as a base. The reaction is carried out at a temperature ranged from 10° C. to 110° C., preferably 40° C. to 70° C., for 1 to 24 hours.

In one further preferred embodiment, the (S)-methylhydroxylaminopropanol compound of formula (II) is reacted with fluoronaphthalene in DMSO by using $KOR_1$ as a base, wherein $R_1$ is $C_{1-6}$ alkyl.

The N,O-cleavage reaction of the N-methyl-N-hydroxyl-3-(1-naphthyloxy)-3-(2-thienyl)propylamine compound of formula (III) in the step (iv) of the process is carried out by hydrogenation in the presence of a catalyst such as Raney-nickel, or by chemical reduction methods such as those using $LiAlH_4$ or zinc metal as reducing agent.

In one preferred embodiment, the N-methyl-N-hydroxyl-3-(1-naphthyloxy)-3-(2-thienyl)propylamine compound of formula (III) is hydrogenated in methanol in the presence of Raney-nickel at a temperature ranged from 15° C. to 80° C., preferably 40° C. to 70° C., for 9 to 15 hours.

Compared with the conventional process, Duloxetine can be obtained optically pure with higher yield and lower cost from the process of the present invention. This process should operate particularly well on an industrial scale having regard to economic and ecological aspects.

EXAMPLES

Example 1

Synthesis of 3-methoxymethylamino-1-(2-thienyl)-1-propanone Hydrochloride Salt

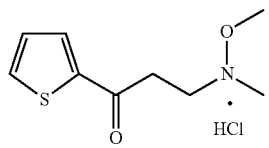

27.7 g of N,O-dimethylhydroxylamine hydrochloride, 9.3 g of paraformaldehyde, 6.4 g of 32% hydrochloride, 30.0 g of 2-acetylthiophene and 100 g of isopropanol were provided into a flask. After being stirred at 60° C. for 13 hours, the reaction mixture was cool down to room temperature. The crystal thus formed was filtered, washed with 30 g of isopropanol and dried under reduced pressure, and then 42.5 g of 3-methoxymethylamino-1-(2-thienyl)-1-propanone hydrochloride salt (75.9%) is obtained. $^1$H NMR (400 MHz, CDCl$_3$) δ (ppm)=3.1 (s, 3H), 3.7-3.8 (br, 4H), 4.1 (s, 3H), 7.2 (t, J=4.5 Hz, 1H), 7.7 (d, J=4.9 Hz, 1H), 7.9 (d, J=3.5 Hz, 1H).

Example 2

Synthesis of (S)-3-methoxymethylamino-1-(2-thienyl)Propan-1-ol

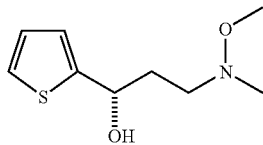

4 mL of degassed methanol solution containing 10 mg of RuCl$_2$((R)-3,5-xylylBINAP) ((2R)-DAIPEN), 160 mg of 3-methoxymethylamino-1-(2-thienyl)-1-propanone, 100 mg of potassium tert-butoxide and 10 mL of methanol were charged in a glass autoclave under an argon gas flow. After deaeration and replacement by argon, hydrogen was introduced to a predetermined pressure. The resulting solution was hydrogenated at 20□ for 12 hours. Upon completion of hydrogenation, the reaction mixture was concentrated, and then the desired compound is obtained as an oily product (161 mg, 95.8% by HPLC assay, 95% ee). $^1$H NMR (400 MHz, CDCl$_3$) δ (ppm)=3.0 (s, 3H), 3.0-3.1 (m, 1H), 4.1 (s, 3H), 4.0-4.1 (m, 3H), 6.1 (dt, J=7.4, 15.4 Hz, 1H), 6.9 (d, J=15.7 Hz, 1H), 7.0 (dd, J=3.7, 5.0 Hz, 1H), 7.1 (d, J=3.4 Hz, 1H).

Example 3

Synthesis of N-methyl-N-methoxyl-3-(1-naphthyloxy)-3-(2-thienyl)Propylamine

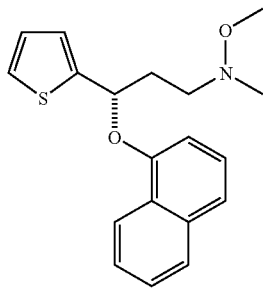 [SMILES: CON(C)CC[C@H](Oc1cccc2ccccc12)c1cccs1]

10.0 g of (S)-3-methoxymethylamino-1-(2-thienyl)propan-1-ol from example 2 was dissolved in 30 mL of N,N-dimethylformamide at ambient temperature, to which was added sodium hydride (3.9 g, 60%) with vigorous stirring. Then, 9.4 g of 1-fluoronaphthalene was added and the mixture was stirred at 70° C. for 8 hours. Upon completion of naphthalenation, the reaction mixture was quenched with water (90 mL). After extraction with toluene (30 mL×3), the organic layer was combined and concentrated. Subsequently, the crude product was purified by silica gel column chromatography to give objective compound as an amber oil (13.5 g, 82.8%). $^1$H NMR (400 MHz, CDCl$_3$) δ (ppm)=2.3 (m, 1H), 2.5 (m, 1H), 2.6 (s, 3H), 2.9 (t, 2H), 3.5 (s, 3H), 5.8 (m, 1H), 6.8 (m, 1H), 6.9 (d, 1H), 7.0 (s, 1H), 7.2 (d, 1H), 7.3 (m, 1H), 7.4 (d, 1H), 7.5 (m, 2H), 7.8 (d, 1H), 8.3 (d, 1H).

Example 4

Synthesis of (S)-(+)-N-methyl-3-methyl-3-(1-naphthyloxy)-3-(2-thienyl)Propylamine (Duloxetine)

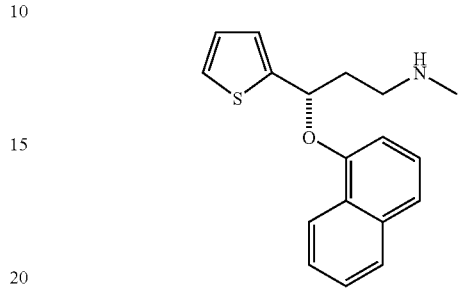

N-methyl-N-methoxyl-3-(1-naphthyloxy)-3-(2-thienyl)propylamine obtained in example 3 was dissolved in 15 mL of methanol with 0.67 g of Raney-nickel charged in a glass autoclave. The resulting solution was hydrogenated at 50□ for 12 hours. Upon completion of hydrogenation, the reaction mixture was filtered and solvent is removed under reduced pressure, and then the desired compound is obtained as an oily compound (12.0 g, 96.4% by HPLC assay). $^1$H NMR (400 MHz, CDCl$_3$) δ (ppm)=2.2 (m, 1H), 2.4 (m, 1H), 2.4 (s, 3H), 2.8 (m, 2H), 5.8 (m, 1H), 6.8 (d, 1H), 6.9 (m, 1H), 7.1 (d, 1H), 7.2 (d, 1H), 7.3 (d, 1H), 7.4 (m, 1H), 7.5 (m, 2H), 7.8 (m, 1H), 8.3 (m, 1H).

Example 5

Naphthalenation of (S)-3-methoxymethylamino-1-(2-thienyl)propan-1-ol with 1-fluoronaphthalene

TABLE 1

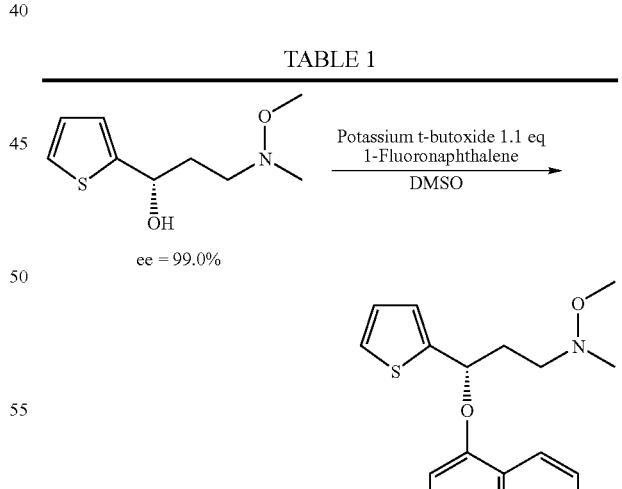

| 1-fluoronaphthalene | 1.5 | 2.5 | 3.0 | 4.0 | 5.0 | 6.0 | 7.0 |
|---|---|---|---|---|---|---|---|
| ee value (%) | 91.1 | 92.5 | 96.2 | 96.3 | 97.1 | 97.3 | 97.4 |

Amount (equivalent)

(S)-3-methoxymethylamino-1-(2-thienyl)propan-1-ol (400 g, 1.987 mole) was dissolved in DMSO (254.3 g) at ambient temperature, to which was added potassium-t-butoxide (245.3 g, 2.186 mole) with vigorous stirring. Then, 1-fluoronaphthalene (1307 g, 7.948 mole) was added, and the mixture was stirred at 50□ for 3-4 hours. Upon completion of naphthalenation, the reaction mixture was cooled to ambient temperature and quenched with water (800 g). After extraction with toluene (1200 mL×3), the organic layer was combined and concentrated. The yield is 82.0% (533.4 g) by HPLC assay. 96.7% of ee value was analyzed by chiral HPLC (DIACELAD-H, 250×4.6 mm ID, (w/w) hexane:IPA:DEA=98:2:0.2, 1 mL/min, UV 248 nm).

Obviously, the ee value (%) was increased with a higher equivalent of 1-fluoronaphthalene. Further, 1-fluoronaphthalene can be removed by extraction and recovered for reuse. Therefore, using a high equivalent of 1-fluoronaphthalene can alleviate the racemization problem without co-solvent system.

The foregoing descriptions of the detailed embodiments are only illustrated to disclose the features and functions of the present invention and not restrictive of the scope of the present invention. It should be understood to those in the art that all modifications and variations according to the spirit and principle in the disclosure of the present invention should fall within the scope of the appended claims.

What is claimed is:

1. A process for preparing a N-methyl-N-hydroxyl-3-(1-naphthyloxy)-3-(2-thienyl) propylamine compound of formula (III),

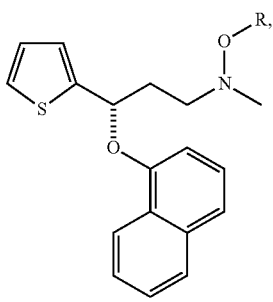
(III)

comprising reacting a (S)-methylhydroxylaminopropanol compound of formula (II)

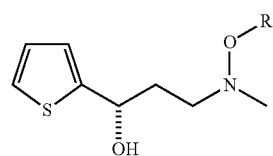
(II)

with $KOR_1$ and halonaphthalene in DMSO,
wherein R is a hydrogen atom, $C_{1-8}$ alkyl or $C_{6-10}$ aryl; $R_1$ is tert-butyl;
and halo is F, Cl, Br or I.

2. The process of claim 1, wherein R is $C_{1-4}$ alkyl.

3. The process of claim 2, wherein R is methyl.

4. The process of claim 1, wherein an amount of the halonaphthalene ranges from 1.5 to 7.0 equivalents based on 1.1 equivalent of the $KOR_1$.

5. The process of claim 1, wherein the process is carried out at a temperature ranged from 10° C. to 110° C.

6. A process for preparing (S)-(+)-N-methyl-3-(1-naphthyloxy)-3-(2-thienyl)propylamine, comprising steps of:
(i) performing a Marmich reaction of 2-acetylthiophene, formaldehyde and a methylhydroxylamine compound of formula, $HNCH_3(OR)$, to form a substituted amino ketone of formula (I),

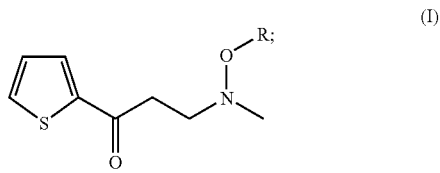
(I)

(ii) reducing the substituted amino ketone of formula (I) enatioselectively to a (S)-methylhydroxylaminopropanol compound of formula (II),

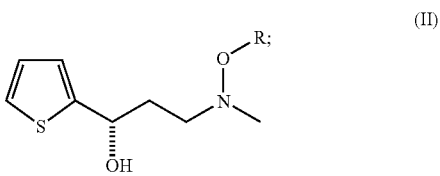
(II)

(iii) reacting the (S)-methylhydroxylaminopropanol compound of formula (II) with $KOR_1$ and halonaphthalene in DMSO to form a N-methyl-N-hydroxyl-3-(1-naphthyloxy)-3-(2-thienyl)propylamine compound of formula (III),

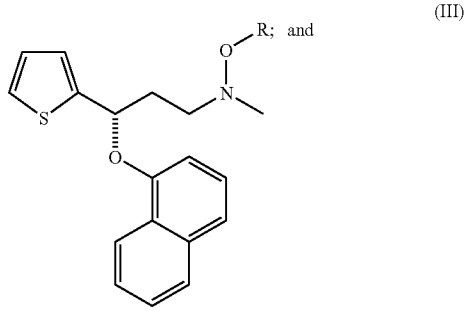
(III)

(iv) performing an N,O-cleavage reaction of the N-methyl-N-hydroxyl-3-(1-naphthyloxy)-3-(2-thienyl)propylamine compound of formula (III) to form (S)-(+)-N-methyl-3-(1-naphthyloxy)-3-(2-thienyl)propylamine,

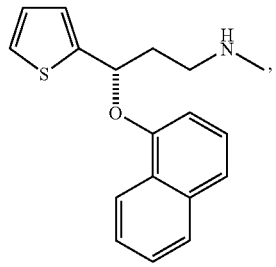

wherein R is a hydrogen atom, $C_{1-8}$ alkyl or $C_{6-10}$ aryl; $R_1$ is $C_{1-6}$ alkyl; and halo is F, Cl, Br or I.

7. The process of claim 6, wherein R is $C_{1-4}$ alkyl.

8. The process of claim 7, wherein R is methyl.

9. The process of claim 6, wherein $R_1$ is butyl.

10. The process of claim 6, wherein an amount of the halonaphthalene ranges from 1.5 to 7.0 equivalents based on 1.1 equivalent of the $KOR_1$.

11. The process of claim 6, wherein the substituted amino ketone of formula (I) obtained in the step (i) is a free form or an acid addition salt.

12. The process of claim 6, wherein the step (ii) is performed by chiral reduction, allowing the (S)-methylhydroxy-laminopropanol compound of formula (II) to be in an optically active form.

13. The process of claim 12, wherein a chiral reducing agent used in the chiral reduction is selected from the group consisting of complex hydride, borane, transition metal catalyst and microbial dehydrogenase.

14. The process of claim 13, wherein a reduction catalyst comprising an enantiomer-enriched bidentate phosphorus-containing ligand, a transition metal and a diamine is used, and wherein the diamine is a chiral diamine.

15. The process of claim 6, wherein the reaction in the step (iii) is carried out at a temperature ranged from 10° C. to 110° C.

16. The process of claim 6, wherein the N,O-cleavage reaction of the N-methyl-N-hydroxyl-3-(1-naphthyloxy)-3-(2-thienyl)propylamine compound of formula (III) in the step (iv) is carried out by hydrogenation in an alcohol in the presence of Raney-nickel at a temperature ranged from 15° C. to 80° C.

17. The process of claim 6, wherein the N,O-cleavage reaction of the N-methyl-N-hydroxyl-3-(1-naphthyloxy)-3-(2-thienyl)propylamine compound of formula (III) in the step (iv) is carried out by a chemical reduction using $LiAlH_4$ or zinc metal as a reducing agent.

18. The process of claim 6, wherein the step (i) is performed at a temperature ranged from 15° C. to 90° C.

19. The process of claim 6, wherein the step (ii) is performed at a pH value ranged from 6 to 14.

* * * * *